United States Patent [19]

Ando

[11] Patent Number: 4,654,035
[45] Date of Patent: Mar. 31, 1987

[54] INJECTOR

[75] Inventor: Yoichi Ando, Yokohama, Japan

[73] Assignee: Mitsubishi Pencil Co., Ltd., Tokyo, Japan

[21] Appl. No.: 775,299

[22] Filed: Sep. 12, 1985

[51] Int. Cl.[4] .............................................. A61M 5/00
[52] U.S. Cl. .................................................. 604/210
[58] Field of Search ................ 604/207, 208, 209, 210

[56] References Cited

U.S. PATENT DOCUMENTS 4,246,898  1/1981  Travalent et al. .................. 604/210
4,444,335  4/1984  Wood et al. ......................... 604/208

Primary Examiner—John D. Yasko
Attorney, Agent, or Firm—Armstrong, Nikaido, Marmelstein & Kubovcik

[57] ABSTRACT

An injector such as a hypodermic syringe and the like is improved in that an amount of injection each time thereof is mechanically determined by provisions of a stopper disconnectably attached to the barrel of the plunger and a plurality of convex/concave portions provided integrally on the outer surface of the plunger and cooperating with the stopper so that the stopper acts as a limiter for an advancing movement of the plunger in the cylinder of the injector to determine the amount of each injection of the injector.

9 Claims, 5 Drawing Figures

INJECTOR

BACKGROUND OF THE INVENTION

1. Field of the Invention

The present invention relates to an improvement of an injector such as a hypodermic syringe and the like.

2. Description of the Prior Art

In a conventional injector, it is troublesome for the user to have to look the scale of the injector in use each time when he confirms an amount of injection of the injector. Further, in case the injection of the injector is performed in a partial manner, it is necessary to stop the advancing movement of the plunger of the injector in its way. However, it is hard to make the plunger stop at a predetermined position of the scale of the injector correctly, so that an error in the amount of the injection is often produced. This is a defect inherent in the conventional injector.

In order to overcome these drawbacks, hitherto many adjustable dosage syringes have been proposed, however, these were unreliable in their strength. The dose syringe must have sufficient strength for their use.

SUMMARY OF THE INVENTION

It is an object of the present invention to provide an injector which has enough strength and makes the user free from a troublesome confirmation of the amount of each individual injection operation of the injector in looking at the scale thereof when the injection operation is performed, particularly in a partial manner, and enables him to accurately infect a uniform quantity in each individual injection operation of the injector without breakage during operation.

The injector of the present invention is characterized in construction in that it includes a stopper, which abuts against a rear end surface of the cylinder of the injector to act as a limiter for advancing movement of the plunger of the injector, is longitudinally movably mounted on an outer peripheral portion of the plunger to be moved in a longitudinal axis of the plunger so that the stopper is fixedly positioned in a predetermined position of the plunger, whereby a prescribed amount of the injection of the injector is easily accomplished by simply pushing forward the plunger until the stopper abuts against the rear end surface of the cylinder.

DETAILED DESCRIPTION OF THE PREFERRED EMBODIMENT

Figure 1:
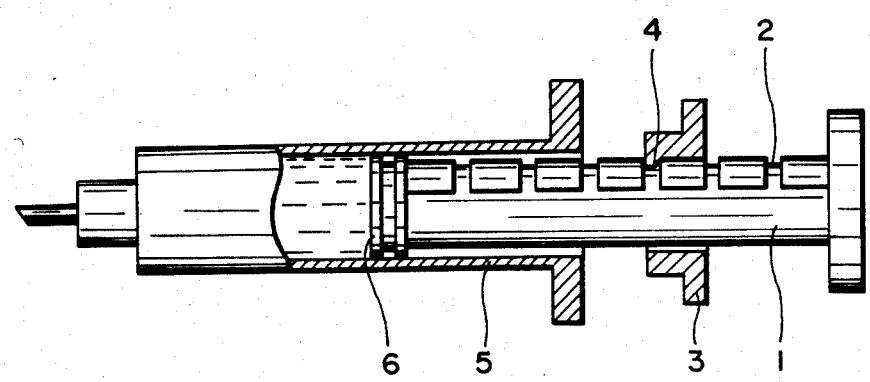
FIG. 1 of the drawings is a partial longitudinal sectional front view of an embodiment of the present invention.

Hereinbelow, an injector of the present invention will be in detail described with reference to the drawing: A plurality of convex/concave portions 2, which are spaced apart from each other at intervals of a certain distance in a longitudinal direction of a circular columnlike plunger 1 of the injector of the present invention, are formed in a row in a portion of an outer peripheral surface of the plunger 1. A stopper 3 having a cylindrical opening is mounted on the outer peripheral surface of the plunger 1 axially and rotatably movable in a circumferential direction of the plunger 1. An inwardly facing projection 4 which has a certain thickness is provided inside the stopper 3 extending partially in a circumferential direction of an inside surface of the stopper 3, so that it is possible to engage disconnectably with the convex/concave portions 2 by rotating the stopper 3 relative to the plunger 1. Under a condition that the projection 4 is connected with the convex/concave portions 2 (more particularly with the concave portion), when the stopper 3 is longitudinally moved relative to the plunger 1 in an axial direction of the plunger 1, the projection 4 is engaged sequentially with each individual convex/concave portions 2 to produce a click noise. Consequently, such a click noise enables the user to know to what extent the stopper 3 is moved on the plunger 1 without looking at a scale on a hollow cylinder 5. However, since it is disadvantageous in use that such a click noise be produced in every movement of the stopper 3, it is necessary to enable the projection 4 to be disconnected from the convex/concave portions 2 by rotating the stopper 3 in a circumferential direction of the plunger 1 relative to the plunger 1 to disengage the projection 4 so that the stopper 3 can be smoothly moved relative to the plunger 1, the operation of which in use is as follows: first, an injection liquid is introduced into the cylinder 5 when the plunger 1, which is fully inserted in the cylinder 5 and to which plunger 1 the stopper 3 has been moved to a rear end of the plunger 1, is partially drawn from the cylinder 5. Next, an injection point of the cylinder 5 is directed upward and then the plunger 1 is smoothly advanced upward relative to the cylinder 5 to discharge any air trapped in the cylinder 5. Thereafter, the stopper 3 is moved and fixedly positioned on the plunger 1 so that an interval between the rear end surface of the cylinder 5 and a front end surface of the stopper 3 is adjusted according to a certain amount of injection of the injection liquid in use of the injector of the present invention. Then, the plunger 1 is simply advanced in the cylinder 5 until the stopper 3 abuts against the cylinder 5 so that the certain amount of injection of the injection liquid is injected successfully. In the drawing, the reference numeral 6 designates a sealing portion of the plunger 1.

Figure 2D:
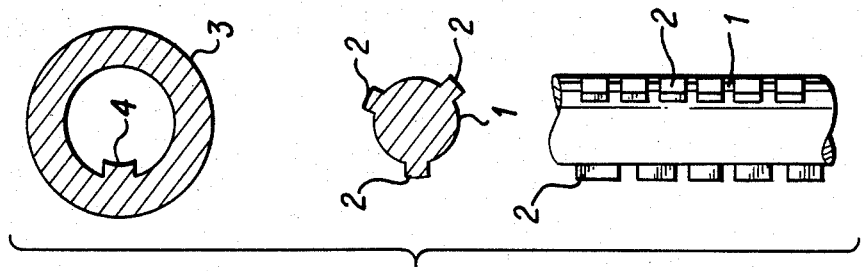
FIGS. 2A, 2B, 2C and 2D show respective partial longitudinal and sectional views of the several embodiments of the invention.
Figure 2C:
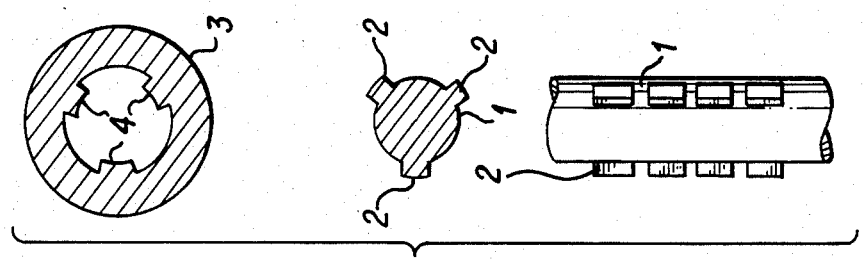
Figure 2B:
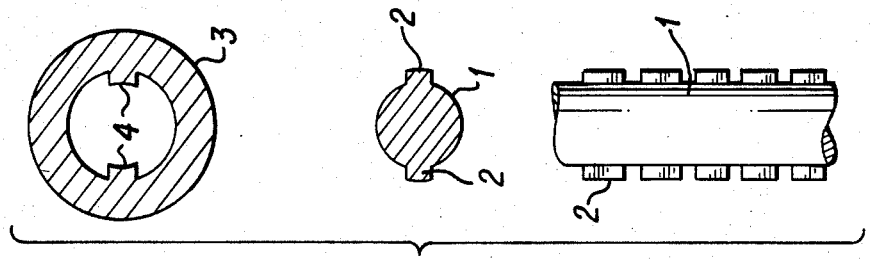
Figure 2A:
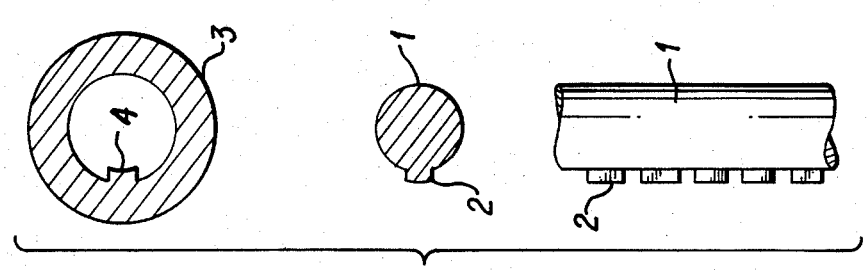

In case the diameter of the plunger 1 is small, it is possible to accomplish the object of the present invention by providing only one row of the convex/concave portions 2 in the longitudinal axis of the plunger 1 as shown in FIG. 2A. On the other hand, the diameter of the plunger 1 is large, it is possible to accomplish the object of the present invention by providing in the longitudinal axis of the plunger 1 two rows of the convex/concave portions 2 which rows are circumferentially spaced at an angle of 180° apart from each other as shown in FIG. 2B and, if necessary three rows of the convex/concave portions 2 which rows are spaced at an angle of 120° apart from each other may be provided as shown in FIG. 2C, whereby it is possible to keep a stopping position of the plunger 1 correctly. In this case, the number of the projections 4 of the stopper 3 is the same as of the rows of the convex/concave portions 2.

Further, in case that a plurality of the rows of the convex/concave portions 2 are provided in the plunger 1, it is possible to finely or largely adjust the amount of the injection by appropriately selecting one of the rows to which one is connected the projection 4 of the stopper 3, provided that the interval of the concave portions of the convex/concave portions 2 in one row thereof is different from that of the concave portions of the convex/concave portions 2 in other row thereof as shown in FIG. 2D, which concave portion is engaged with the projection 4 of the stopper 3. In this case, it is natural that the number of the projections 4 of the stopper 3, which projection 4 is connected to the concave portion of the convex/concave portions 2, is one in contrast with the preceding case.

Incidentally, in the above embodiment, a mounting position of the stopper 3 on the plunger 1 is adjusted by changing a connecting position of the projection 4 of the stopper 3 and the convex/concave portions 2 of the plunger 1. However, it is possible to provide another embodiment (not shown) of the present invention in which embodiment the mounting position of the stopper 3 on the plunger 1 is adjusted by rotating the stopper 3 relative to the plunger 1 to be moved forward or rearward through a threadable connection of screw portions which mesh with each other and are provided inside the stopper 3 and in the outer peripheral surface of the plunger 1, respectively, whereby a fine adjustment of an amount of injection of the injector of the present invention can be conducted.

Furthermore, it is also possible to mount the stopper 3 on the plunger 1 by means of a spring and the like.

The injector of the present invention may be made of any suitable materials, provided that they satisfy the requirements for the conventional injector such as the hypodermic syringe and the like, for example, a requirement for strength and a requirement for chemical stability that they do not react with the injection liquid and other similar requirements.

Since the injector of the present invention is constructed as mentioned above, the injector of the present invention has an effect that it enables the user to easily and correctly conduct a prescribed amount-injection operation by simply advancing the plunger 1 in the cylinder 5 until the stopper 3 having been previously positioned in a suitable position according to the amount of the injection abuts against the cylinder 5 without necessity for confirmation of an amount of the advancing movement of the plunger 1 in the cylinder 5 by looking the scale of the cylinder 5. Further, the injector of the present invention has an advantage in that it is possible to appropriately change the adjusting degree of the amount of the injection even with the use of one injector of the present invention.

More particularly, the injector of the present invention has a remarkable effect in conducting its injection operation in a partial manner in which the advancing movement of the plunger 1 must be stopped in its way periodically.

What is claimed is:

1. An injector comprising:
   a hollow cylinder having an injection point at one end and a rear end surface at another end thereof;
   a circular column-like plunger having a sealing portion at an end thereof fitted to the inside of said hollow cylinder for axial movement therein;
   a plurality of convex/concave spaced apart portions formed in a row extending in an axial direction on an outer peripheral surface of said plunger; and
   a stopper member arranged to engage said rear end surface of said hollow cylinder and having a cylindrical opening therein, said stopper member being mounted on said outer peripheral surface of said plunger for axial and rotational movement thereon and being provided at said opening with at least one inwardly facing projection extending over a portion of its inner circumference so as to engage said convex/concave portions of said plunger;
   said stopper member being rotatably movable to a position whereat said projection does not engage a convex/concave portion of said plunger and in such position being axially movable on said plunger without rotation to a position whereat said projection is adjacent a selected convex/concave portion, and then rotatably positioned so that said projection will engage said selected convex/concave portion to thereby set a limit on axial movement of said plunger in said cylinder.

2. An injector as recited in claim 1, wherein said plunger is formed with a plurality of circumferentially spaced rows of said axially extending convex/concave portions.

3. An injector as recited in claim 2, wherein the member of said rows is two.

4. An injector as recited in claim 2, wherein the number of said rows is three.

5. An injector as recited in claim 2, wherein said stopper member is provided with a number of inwardly facing projections equal to the number of said plurality of rows of convex/concave portions.

6. An injector as recited in claim 3, wherein said stopper member has two inwardly facing projections.

7. An injector as recited in claim 4, wherein said stopper member has three inwardly facing projections.

8. An injector as recited in claim 2, wherein said convex/concave portions of each of said plurality of circumferentially spaced rows of axially extending spaced apart convex/concave portions are spaced at different intervals, and said stopper is provided with a single inwardly facing projection, said stopper being rotatably movable to engage said projection with a selected row of convex/concave portions.

9. An injector as recited in claim 1, wherein said stopper, when positioned so that said projection will engage said row of convex/concave portions, may be moved relative to the plunger in an axial direction to cause said projection to produce a click noise as it engages sequentially with each of said spaced apart convex/concave portions.

* * * * *